United States Patent [19]

Werle et al.

[11] Patent Number: 5,352,841
[45] Date of Patent: Oct. 4, 1994

[54] AGENT FOR DOSING AQUEOUS SYSTEMS WITH ACROLEIN, PROCESSES FOR MAKING SAME, AND METHOD OF TREATING AN AQUEOUS SYSTEM

[75] Inventors: Peter Werle, Gelnhausen; Werner Pahling, Karben; Martin Trageser, Gelnhausen, all of Fed. Rep. of Germany

[73] Assignee: Degussa Aktiengesellschaft, Frankfurt, Fed. Rep. of Germany

[21] Appl. No.: 165,922

[22] Filed: Dec. 14, 1993

[30] Foreign Application Priority Data

Sep. 24, 1993 [DE] Fed. Rep. of Germany ....... 4332586

[51] Int. Cl.$^5$ .................... C07C 45/78; C07C 45/00
[52] U.S. Cl. ..................... 568/449; 568/421
[58] Field of Search ............... 514/646; 568/421, 465, 568/468, 449

[56] References Cited

U.S. PATENT DOCUMENTS

| | | | |
|---|---|---|---|
| 2,959,476 | 11/1960 | Overb | 568/449 |
| 3,250,667 | 5/1966 | Legator | 568/463 |
| 3,878,250 | 4/1975 | Sato et al. | 568/421 |
| 4,851,583 | 7/1989 | Bockowski | 568/465 |
| 5,183,944 | 2/1993 | Werle et al. | 568/465 |

FOREIGN PATENT DOCUMENTS

| | | |
|---|---|---|
| 4038471 | 6/1992 | Fed. Rep. of Germany . |
| 2042536 | 9/1980 | United Kingdom . |

*Primary Examiner*—Werren B. Lone
*Attorney, Agent, or Firm*—Beveridge, DeGrandi, Weilacher & Young

[57] ABSTRACT

Liquid acrolein, whose hazardous properties make handling difficult, is used to dose aqueous systems with acrolein in a biocidally effective concentration. Disclosed are agents which increase the ease and safety of acrolein handling and which are characterized by a content of 30 to 95% by weight acrolein and 5 to 70% by weight inorganic carrier materials. Silicas are the preferred carrier materials. The powdery or highly viscous mixture of substances will preferably exist in molded form and is additionally provided with a cladding that is impermeable to acrolein vapor. In dosing the aqueous systems, the agents are introduced directly in the water whereupon the acrolein is released.

23 Claims, No Drawings

AGENT FOR DOSING AQUEOUS SYSTEMS WITH ACROLEIN, PROCESSES FOR MAKING SAME, AND METHOD OF TREATING AN AQUEOUS SYSTEM

INTRODUCTION AND BACKGROUND

The present invention relates to an agent for dosing aqueous systems with acrolein in concentrations effective as a biocide to prevent the growth of algae, aquatic weeds, and mucous. The present invention also concerns processes for producing such agents and a method of treating aqueous systems to control aquatic life by utilizing such agents.

Acrolein is a well-known biocide for treating liquids, particularly aqueous solutions in open and closed circulating systems containing muciferous microorganisms. The biocidal effectiveness of acrolein is directed to the prevention, regulation, and destruction of microorganisms in the group of bacteria, viruses, fungi, and algae; its high effectiveness permits acrolein of low concentrations to be used in water (U.S. Pat. Nos. 2,959,476 and 3,250,667, both of which are incorporated by reference in their entirety).

Due to its ability to quickly terminate photosynthesis, not only in algae but in larger celled aquatic weeds, and to thereby kill them, acrolein is used to combat weeds in water channels and to prevent the stoppage of pump systems. In addition, for years it has been a proven interceptor of hydrogen sulfide since it can both irreversibly bind $H_2S$ and eliminate the source of $H_2S$ by killing sulfate-reducing bacteria (e.g., *Desulvovibrio desulfuricans*).

Despite the high biocidal effectiveness of acrolein, its hazardous properties work against a broad application. Acrolein is poisonous and toxic when inhaled, causes choking and tearing, and is slightly flammable (flash point $-29°$ C., boiling point $53°$ C.), which makes its handling difficult and expensive. Moreover, the contamination of acrolein with impurities also creates the danger of explosive polymerization. There has been no lack of proposals to reduce the potential hazard posed by contact with acrolein.

U.S. Pat. No. 4,851,583 suggests the use of an acrolein acetal instead of acrolein and the catalytic hydrolysis of acrolein acetal into acrolein. This process is not suitable for dosing flowing water since it would rapidly result in the contamination or deactivation of the employed ion exchanger.

DE 40 38 471 (U.S. Pat. No. 5,183,944) describes a process in which acrolein is released from cyclical acetals through the addition of a protonic acid with the simultaneous application of heat and reduced pressure or the introduction of nitrogen. Acrolein is removed in gaseous form and is introduced in that form into the medium being dosed out. DE 43 26 575.8 discloses an embodiment for dosing irrigation channels through the use of an acrolein acetal which does not rely on the availability of electronic of energy.

All prior art processes for dosing aqueous systems on the basis of an acrolein acetal also have the disadvantage that acetal, which is produced from acrolein, is considerably more expensive than acrolein.

SUMMARY OF THE INVENTION

An object of the present compound is to provide an agent that is suitable for dosing aqueous systems, which is less difficult to handle than liquid acrolein, and does not exhibit the disadvantages associated with the use of acrolein acetal.

In attempting the above and other objects, one feature of the present invention resides in an agent for the dosing of aqueous systems with acrolein in a biocidally effective concentration comprising an acrolein content of 30 to 95% by weight and 5 to 70% by weight of one or more inorganic carrier materials that are basically inert relative to acrolein and which exhibit a pH value of 3 to 7 in a 5% dispersion in water.

Another object of the present invention is to provide processes for the production of such agents involving mixing acrolein and inorganic carrier material to form a mixture, homogenizing the mixture, optionally converting the homogenized mixture into a molded body, and optionally enclosing the molded body with a cladding material. Alternatively, the process involves converting the inorganic carrier material to a pressed piece, applying acrolein to the pressed piece, and optionally enclosing the pressed piece with a cladding material.

Yet another object of the present invention is to provide a method of treating aqueous systems to control aquatic life by dosing the agent described herein into the aqueous system in a biocidally effective concentration.

DETAILED DESCRIPTION OF THE INVENTION

According to the present invention there is provided an agent for the dosing of aqueous systems in order to prevent the growth of algae, aquatic weeds and mucous. The agent preferably exhibits a solid, more or less powdery consistency; naturally, the agent may also exist in molded form, e.g., granules, tablets, pellets, eggs, briquettes, or other pressed and shaped pieces. In the case of a very high acrolein content, e g , 85% to 95% by weight, the agent may be moist and crumbly or highly viscous, and possibly gelatinous. With the carrier of the present invention, the mixture is surprisingly stable during storage.

Any leakage from damaged drums or apparatus, which can lead to considerable problems when acrolein is present in a form with low viscosity and a low boiling point, is not critical given the consistency of the agent according to the present invention since it is easily absorbed and used for its intended purpose. Any local contamination of the agent with impurities is less critical than is the case with liquid acrolein, particularly when the agent is present in molded form, since the carrier material has a stabilizing effect, and any spread of disruptive effects is reduced by the molded and preferably encapsulated agent. When the agent is introduced into water, acrolein is released completely and is available as a biocide without the need for special processes or apparatus as is the case with acrolein acetals.

The carrier may consist of one or a plurality of substances; a single substance is preferred. The pH value of a 5% dispersion of the carrier in water must not be more than 7 since acrolein is able to polymerize in the alkaline range. The pH value preferably lies between 5 and 7, particularly between 5 and 6.5, and the pH value can be determined according to DIN (German Industrial Standard) ISO 787/IX or ASTM D1208. The carrier surface area determined according to BET (DIN 66131) is preferably between 100 and 700 $m^2/g$, particularly between 150 and 700 $m^2/g$. The statement "basically inert relative to acrolein" is understood to mean that the carrier does not induce polymerization of the acrolein, but that a partial reaction of acrolein with functional groups on the surface of the carrier, e.g., hydroxyl or carboxyl groups, is not excluded.

In principle, all carriers which exhibit an adequate absorptive capability for acrolein and satisfy the above criteria can be utilized in the present invention. Preferred carriers have an oxidic or silicate structure; the required pH value may also be achieved by treating the carrier with an acid—for example, $TiO_2$ with phosphoric acid, followed by heat treatment and washing. Particularly suited carriers are pyrogenic and precipitated silicas and neutral to acidic silicates, including zeolites, particularly dealuminized Y-zeolites.

A preferred embodiment of the agent basically consists of 40 to 85% by weight acrolein, 60 to 15% by weight of one or several silicas or silicates with a BET area of 150 to 700 $m^2/g$ and a pH value of 5 to 7 in a 5% dispersion, and an effective quantity of one or several conventional stabilizers for acrolein, preferably hydroquinone, in a quantity between 100 and 5000 ppm. The term "basically" means that in addition to conventional impurities of commercial acrolein and the carrier, specifically water in a quantity up to 3% by weight relative to the total of acrolein and the carrier, there may also be present treatment adjuvants, e.g., a tablet dispersing agent, in a quantity up to 3% by weight relative to the total of acrolein and carrier, as well as a cladding material for enclosing the molded pieces and providing further protection and easily handling. The cladding material may be a film forming natural or synthetic polymer.

According to a preferred embodiment the agent is present in the form of molded bodies or pieces with a solid or gelatinous consistency and exhibits a cladding that is basically impermeable to acrolein. The mass of the piece may typically range from 0.1 g to 4–5 kg although larger masses are possible. Preferably the molded bodies have a mass between 0.2 g and 200 g, particularly between 1 g and 50 g. The cladding facilitates safe handling and reduces the danger of contamination.

To use the agent, the cladding, e.g., a welded film, can either be removed or perforated to permit the penetration of water.

According to a specially preferred embodiment, the molded pieces mentioned above are enclosed by a cladding material that though largely impermeable to acrolein vapor is nonetheless soluble in water. This assures safe handling since the acrolein contained in the agent is only released once the enclosed agent has been introduced into the water and the cladding has begun to dissolve. A specially suited water soluble, cladding material is gelatine, particularly soft gelatine. Polyalkylene are other suitable water-soluble or penetrable cladding materials. These are substances well known in the art and any suitable substance of this nature can be used. Alternatively, the cladding material (e.g., paraffin wax) may be largely impermeable to acrolein vapor and insoluble in water.

The cladding process may expediently proceed by means of a thin film of the cladding material, which is welded all the way around, or by means of a coating process. In the case of a powdery mixture molded into a pressed piece or a highly viscous mixture of acrolein, carrier, and any adjuvants, the agent can be cladded or encapsuled by means of conventional encapsulation techniques.

When a water-insoluble cladding is used, it is expedient to design the cladding in such a way that it becomes penetrable to water immediately before use for dosing into the aqueous system, for example by perforation or by opening devices within the cladding.

Agents with a highly viscous consistency may also be enclosed in a pressure container or in cartridges from which they are directly introduced into the aqueous system.

To produce the agent according to the present invention there are two alternative processes:

(1) Production of an homogeneous mixture of acrolein, carrier, and, when desirable or necessary, adjuvants, in a mixing device for intensive mixing; this is followed, when so desired, by conversion of the mixture into molded pieces, for example, pressed pieces, and/or cladding by means of conventional coating, encapsulating, or other cladding techniques, or introduction into a pressure container or cartridges. If the mixture of substances is compressed after homogenization, it is recommended that the acrolein concentration be limited according to the pressure applied by the molding device, usually to 30 to 40% by weight, so that acrolein is not removed in the pressing process.

(2) Pressed piece are produced in a known manner from carrier materials in powder form, when necessary with the use of a parting, baking, and tablet-dispersing agent; acrolein is then applied to the pressed piece, preferably in a quantity such that afterwards the pressed pieces are dry to the touch. Here too a further step may consist in cladding the pressed pieces, for example, by immersion in a bath containing the cladding material or by spraying the cladding material in liquid form or by means of welding a film.

The agents according to the present invention can be used for dosing into aqueous systems, particularly hydraulic circuits, irrigation channels, and oil field water. The agents, which can be easily handled, are simply introduced into the water, whereupon the acrolein is released. The carrier is inert and does not pose problems to the system being treated. As already indicated, when agents are used whose claddings are insoluble in water, the cladding must be made penetrable to water before use, or must be removed. A biocidally or herbicidally effective concentration of acrolein is easily determined by standard methods known in the art.

It could not be foreseen that agents which are stable during storage, and are in many respects easier and safer to handle than acrolein, could be created by means of the absorption of acrolein by a carrier material. These advantages are considerably enhanced by agents exhibiting a cladding, particularly one of material that is sealed against acrolein vapor and is water-soluble, inasmuch as such agents are largely insensitive to unintentional contamination and are basically odor-free.

EXAMPLE 1

50 g of a precipitated silica with characteristic data pH 6.5; BET surface area 450 $m^2/g$, commercially available as Sipernat 50 (Degussa) are mixed with 117 g acrolein that has been stabilized with 1100 ppm hydroquinone. The result is 167 g of a finely flowing powder. The acrolein content is 70% by weight.

EXAMPLE 2

50 g of a precipitated silica with characteristic data pH 7.0; BET surface area 650 $m^2/g$ (commercial product Sipernat FK 310, Degussa) are mixed with 93 g stabilized acrolein. The result is 143 g of a finely flowing powder with an acrolein content of 65% by weight.

EXAMPLE 3

75 g of a silicon dioxide produced by high temperature hydrolysis with characteristic data pH approx. 4; BET surface area 200 m$^2$/g (commercial product Aerosil 200, Degussa) are mixed with 425 g stabilized acrolein. The result is 500 g of a translucent-opaque body with a rubbery, pumpable consistency and with an acrolein content of 85% by weight.

EXAMPLE 4

The acrolein-silica mixture from example 1 is encapsulated in a commercially available hard gelatine capsule in a capsule-filling apparatus (Roebiger Co., Berlin). The resulting capsules, which are practically odorless, are stable during storage. After adding the capsule to water the capsule dissolves within about one hour and the acrolein is released.

EXAMPLE 5

5.0 g of a precipitated silica are pressed with a hand press at 5 t pressure to form a tablet. Dripping 5.5 g acrolein onto this tablet provides an agent with an acrolein content of 52% by weight. A water-tight coating can be applied by immersing the cooled tablet in liquid paraffin wax.

EXAMPLE 6

19.5 g stabilized acrolein are dripped onto 30 g of a dealuminized Y-zeolite of nominal width 7.4 Å, pH 4.5, module 200, that has a cylindrical shape. The result is an visually dry granulate of 30% by weight.

Further variations and modifications of the foregoing will be apparent to those skilled in the art and such variations and modifications are attended to be encompassed by the claims that are appended hereto.

German Priority Application P 43 32 586.6, filed on Sep. 24, 1993, is relied on and incorporated by reference.

What is claimed:

1. An agent for dosing aqueous systems with acrolein in a biocidally effective concentration comprising 30 to 95% by weight of acrolein and 5 to 70% by weight of at least one inorganic carrier material, wherein said inorganic carrier material is basically inert relative to acrolein and has a pH value of 3 to 7 in a 5% dispersion in water.

2. The agent according to claim 1, wherein said pH value is between 5 and 7.

3. The agent according to claim 2, wherein said pH value is between 5 and 6.5.

4. The agent according to claim 1, wherein said carrier material exhibits a BET surface area of 100 to 700 m$^2$/g.

5. The agent according to claim 4, wherein said carrier material exhibits a BET surface area of 150 to 700 m$^2$/g.

6. The agent according to claim 1, wherein said carrier material has an oxidic or silicate structure.

7. The agent according to claim 6, wherein said carrier material is pyrogenic and precipitated silica or neutral to acidic silicate.

8. The agent according to claim 7, wherein said carrier material is a zeolite.

9. The agent according to claim 8, wherein said zeolite is a dealuminized Y-zeolite.

10. The agent according to claim 1, wherein said agent comprises 40 to 85% by weight acrolein, 60 to 15% by weight of at least one silica and/or silicate which exhibit a BET surface area of 150 to 700 m$^2$/g and a pH value of 5 to 7 in a 5% dispersion in water, and an effective quantity of at least one acrolein stabilizer.

11. The agent according to claim 10, wherein said stabilizer is hydroquinone in a quantity between 100 and 5000 ppm.

12. The agent according to claim 1, wherein said agent further comprises a tablet dispersing agent in a quantity up to 3% by weight relative to the total of said acrolein and said carrier.

13. The agent according to claim 1, wherein said agent exhibits a solid consistency and takes the form of molded pieces.

14. The agent according to one of claim 1, wherein said agent is present in the form of molded, solid or gelatinous pieces which are enclosed by a cladding material which is water-soluble or penetrable by water or is water-insoluble, wherein said cladding material is basically impermeable to acrolein vapor.

15. The agent according to claim 14, wherein the mass of said pieces is at least 0.1 g.

16. The agent according to claim 15, wherein the mass of said pieces ranges from 0.2 g to 200 g.

17. The agent according to claim 16, wherein the mass of said pieces ranges from 1 g to 50 g.

18. The agent according to claim 14, wherein said cladding material is gelatin, paraffin wax, or polyalkylene.

19. A process for producing the agent according to claim 1, said process comprising mixing said acrolein and said carrier material to form a mixture, homogenizing said mixture, optionally converting said homogenized mixture into a molded body, and optionally enclosing said molded body with a cladding material.

20. A process for producing the agent according to claim 1, said process comprising converting said carrier material to a pressed piece, applying acrolein to said pressed piece, and optionally enclosing said pressed piece with a cladding material.

21. A method of treating an aqueous system to control aquatic life comprising dosing the agent according to claim 1 into said aqueous system in a biocidally effective concentration.

22. The method according to claim 21, wherein said agent is present in the form of molded, solid or gelatinous pieces which are enclosed by a cladding material which is water-soluble or penetrable by water or water-insoluble, wherein said cladding material is basically impermeable to acrolein vapor.

23. The method according to claim 22 further comprising removing or perforating said water-insoluble cladding material to permit the penetration of water.

* * * * *